United States Patent [19]

Baltz et al.

[11] Patent Number: 5,450,742
[45] Date of Patent: Sep. 19, 1995

[54] METHOD AND APPARATUS FOR DYNAMIC TESTING OF A DEVICE

[75] Inventors: Rolf Baltz, Bruckmühl; Franzjosef Unterberg, Riemerling; Franz Patzelt, Taufkirchen, all of Germany

[73] Assignee: Industrieanlagen-Betriebtgesellschaft mbH, Ottobrunn, Germany

[21] Appl. No.: 117,178
[22] PCT Filed: Feb. 26, 1992
[86] PCT No.: PCT/EP92/00401
§ 371 Date: Jan. 28, 1994
§ 102(e) Date: Jan. 28, 1994
[87] PCT Pub. No.: WO92/15856
PCT Pub. Date: Sep. 17, 1992

[30] Foreign Application Priority Data

Mar. 4, 1991 [DE] Germany .......... 41 06 787.8
Feb. 8, 1992 [DE] Germany .......... 42 03 709.3

[51] Int. Cl.$^6$ .................................................. G01N 3/30
[52] U.S. Cl. ................................. 73/12.06; 73/12.05
[58] Field of Search ............... 73/12.05, 12.06, 71.6, 73/67.1, 12, 1 D; 360/75

[56] References Cited

U.S. PATENT DOCUMENTS

| | | | |
|---|---|---|---|
| 2,763,148 | 9/1956 | Hoppmann II | 73/12.06 |
| 3,100,982 | 8/1963 | Cutler | 73/12.06 |
| 3,106,834 | 10/1963 | Parstorfer | 73/12.06 |
| 3,226,974 | 1/1966 | Bresk et al. | 73/12.06 |
| 3,304,773 | 2/1967 | Rogallo | 73/12.05 |
| 3,426,578 | 2/1969 | Bergs et al. | 73/12 |
| 3,535,912 | 10/1970 | Muller | 73/12 |
| 3,538,743 | 11/1970 | Glidden | 73/12.06 |
| 3,750,457 | 8/1973 | Pascquet | 73/12 |
| 4,433,570 | 2/1984 | Brown et al. | |

FOREIGN PATENT DOCUMENTS

| | | | |
|---|---|---|---|
| 0314829A1 | 11/1987 | European Pat. Off. | G01N 3/30 |
| 6934387 | 9/1969 | Germany . | |
| 63-113342 | 5/1988 | Japan | G01N 3/30 |
| 63-284451 | 11/1988 | Japan | G01N 3/30 |
| 1085064 | 9/1967 | United Kingdom | G01N 3/30 |

Primary Examiner—Richard E. Chilcot, Jr.
Assistant Examiner—Jewel V. Artis
Attorney, Agent, or Firm—Seed and Berry

[57] ABSTRACT

A method of dynamically testing the functionality of a multi-part specimen comprises the steps of applying a predetermined reproducible shock loading to one part of the specimen and measuring the resulting shock load both at the point of application on said one part and at at least one point on another part of the specimen. Said measured shock loads are also recorded. Apparatus for carrying out this method comprises a drop carriage with means for coupling to one part of the specimen, and at least one acceleration transducer for attachment to the drop carriage and also to at least one part of the test specimen. The apparatus thus produces reproducible shocks up to 40,000 g to enable the structural optimization of severely shock-loaded articles such seat-belt buckles and their functionality both during and after the shock-loading to be demonstrated.

11 Claims, 2 Drawing Sheets

METHOD AND APPARATUS FOR DYNAMIC TESTING OF A DEVICE

TECHNICAL FIELD

The present invention relates to a method and apparatus for dynamically testing multi-part articles by subjecting them to severe shock. In particular, the invention relates to a method and apparatus for subjecting seat-belt buckles which are operatively associated with inertial-reel tightening mechanisms to severe shock.

BACKGROUND OF THE INVENTION

When such seat belts are in use and an automobile crash occurs, the belt tightener such as the inertial-reel, which as a rule is mounted on the floor or on the seat of the automobile, very rapidly pulls against the component by which the buckle is fixed, ordinarily called the stalk, so that the normally loose seat belt is stretched tight. In this tightening process, the individual elements of the buckle assembly, namely the stalk, the locking element and the tongue, are subjected to a high shock loading. However, the buckle assembly must be constructed so that this shock loading does not cause any malfunction; the buckle must remain reliably closed during the shock loading that accompanies the tightening process and during the subsequent loading by the tensile stress imposed on the belt as it restrains the seat occupant. Afterward the buckle must be easy to open.

In tests of buckle function, therefore, a distinction must be made between the high-energy shock loading during the tightening process and the loading during restraint of the occupant.

The present method and associated testing apparatus relate exclusively to the high-energy shock testing.

In the present state of the art of testing the buckles of seat belts equipped with tightening mechanisms, it is characteristic that for every series of tighteners and associated buckles, the reliable locking function of the buckle is tested by triggering the tightener in a statistically sufficient number of units in the series.

In such methods only nominal loads for the particular type of construction are imposed, but no overloading. However, overloading is necessary to determine the actual functional limits of the buckle or to build in and demonstrate the safety factor desired for specific ranges of overloading.

The problem to be solved thus consists of two closely related subproblems:

First, the shock loading must be quantitatively monitored and controlled separately for each component of the functional assembly in order to obtain absolute load values for each component and to measure quantitatively the distribution of shock in the various components according to their structural relationships in the assembly.

Second, reliably reproducible experimental conditions must be ensured for acceleration amplitudes greater by as much as 3- to 4-fold than the loads that actually occur in practice.

The current state of the art of shock production for test objects of the nature and size of seat-belt buckles is characterized by apparatus in which a cable-guided carriage is dropped through a frame, as described in principle in U.S. Pat. No. 3,426,578 and German Gebrauchsmuster DE-GM 69 34 387. Such conventional drop-frame apparatus provides for shocks of up to ca. 10,000 g to be imposed over times in the range of $\mu s$, depending on the drop distance, the mass and shape of the drop carriage, the material and the impact medium. Alternatively, for lower shock accelerations, an oscillating-hammer test stand can be used, such as is described in Japanese Patent Specification JP 63-11 33 42 A. A sensor for shock measurement is mentioned in Japanese Patent JP 63-28 44 51 A, but it is not attached to the drop carriage or to the specimen to be tested, but rather to a neutral intermediate element.

When the peak acceleration is increased by 3- to 4-fold, however, the drop carriage itself can be set into oscillation, which interferes with the measurement and makes it impossible to ensure reproducibility of the shock, so that the range of application is limited. Furthermore, after a few shocks the impact surface of the carriage becomes deformed and develops cracks, which makes the carriage unsuitable for further use. The same applies to the impact medium, onto which the carriage falls.

Constructional means of reducing the intrinsic oscillations of the drop carriage and indications of the shape and selection of material of the drop carriage for the load values required here are not disclosed in the literature of the field.

Thus, the object of the present invention is to provide a method and an associated testing apparatus for a functional assembly that enables rapid, simple and relatively inexpensive reproduction of both the shock loads typically encountered in operation of the assembly and overloads for the applications described above in a manner wherein the shock loads are imposed in a quantitative and reliably reproducible manner.

SUMMARY OF THE INVENTION

According to a first aspect of the present invention there is provided a method of dynamically testing the functionality of a multi-part specimen comprising the steps of applying a predetermined reproducible shock loading to one part of the specimen, and measuring the resulting shock load, and wherein the improvement comprises the measurement of said resulting shock load both at the point of application on said one part and at at least one point on another part of the specimen, and the recordal of said measured shock loads.

According to a second aspect of the present invention there is provided apparatus for dynamically testing the functionality of a multi-part specimen by the application of a predetermined, reproducible shock loading thereto comprising a drop carriage with means for coupling to one part of the specimen, and wherein the improvement comprises the provision of at least one acceleration transducer for attachment to the drop carriage and also to at least one part of the test specimen.

Preferably, the apparatus additionally comprises a signal-processing system for the recordal, processing and display of output signals from said at least one acceleration transducer.

BRIEF DESCRIPTION OF THE DRAWINGS

The various aspects of the present invention will now be described by way of example with reference to the accompanying drawings, in which.

DETAILED DESCRIPTION OF THE INVENTION

Figure 1:
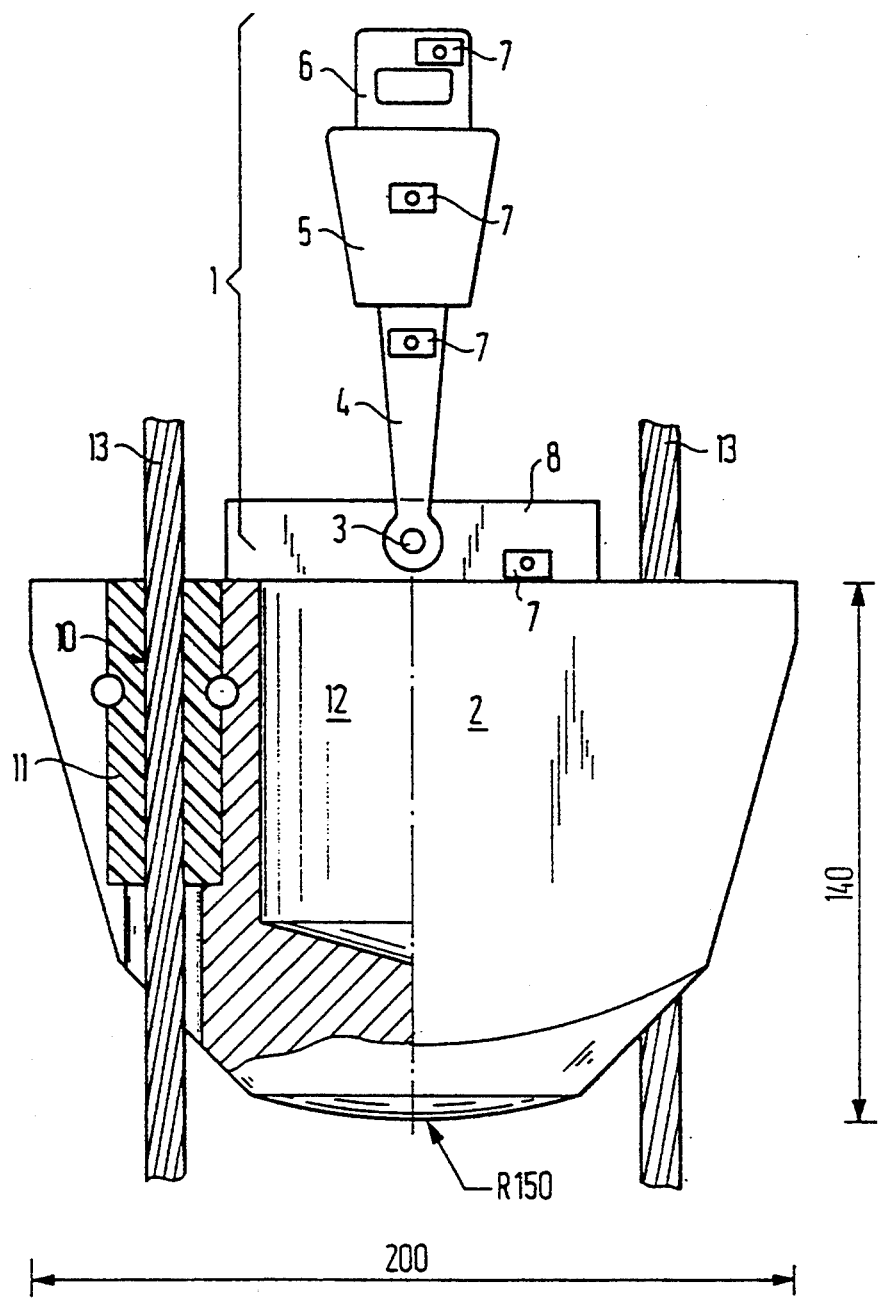
FIG. 1 is a front elevation of an apparatus according to the invention with a test specimen mounted thereon.

The apparatus comprises a drop-frame apparatus with a drop carriage 2 comprising cable guides 10 with slide bushes 11 through which a guide cable 13 passes. A reproducibly high shock load is determined by the shape and the material selected for the drop carriage 2 and by the material selected for an impact medium 14 on the base as will be described.

A test specimen 1 is attached, for example by means of a threaded joint 3, either directly to the drop carriage 2 or, for ease of assembly, to an adapter 8 screwed to the drop carriage 2. The test specimen 1 such as a seat-belt buckle typically comprises several functional components 4, 5 and 6, to each of which at leash one acceleration transducer 7 is attached. The drop carriage 2 also bears an acceleration transducer 7 as shown in FIG. 1.

With this arrangement of the acceleration transducers 7, the base shock can be monitored quantitatively as well as the shock effects induced in each of the functional components 4, 5, 6. In addition, where required shock-transfer behavior can be analyzed and structural means can be designed by which to eliminate identified weak spots or optimize the test specimen with respect to its shockproof functionality.

The drop carriage 2 itself is compact, being made integrally in substantially one-piece with integral cable guides 10; it is conical in shape and substantially symmetrical over 180° about its vertical axis in order to minimize wobbling.

Despite the shape of the drop carriage 2, its center of gravity is shifted downward towards the impact surface to a considerable extent by the provision of a cavity 12 in the upper part of the drop carriage 2. This tends to reduce tilting of the carriage on impact. The impact surface of the carriage 2 is rounded and defines a part-spherical section with a radius R of ca. 150–200 mm, as shown in FIG. 1. The mass of the drop carriage 2 and its structural dimensions are very much dependent on the intended application of the apparatus. For the present application in the testing of seat-belt buckles, the mass is ca. 10 kg and the dimensions are as indicated in FIG. 1. The highly specialized material requirements of the drop carriage with respect to hardness, toughness, and the avoidance of cracking and flattening of the impact surface in long-term use are satisfied by constructing same of a low-alloy, high-strength tempered steel, for example one conforming to Classification 1.6959 of DIN (Deutsche Industrie Norm) Standard 17 007. The impact medium 14 is a consumable element, which for rapid and economical exchange can, for example, be constructed as a disk in a disk holder or as a rapidly exchangeable block of high-carbon structural steel.

The lifting, fastening and releasing devices used in connection with the drop-frame apparatus are conventional and are not described herein.

Figure 2:
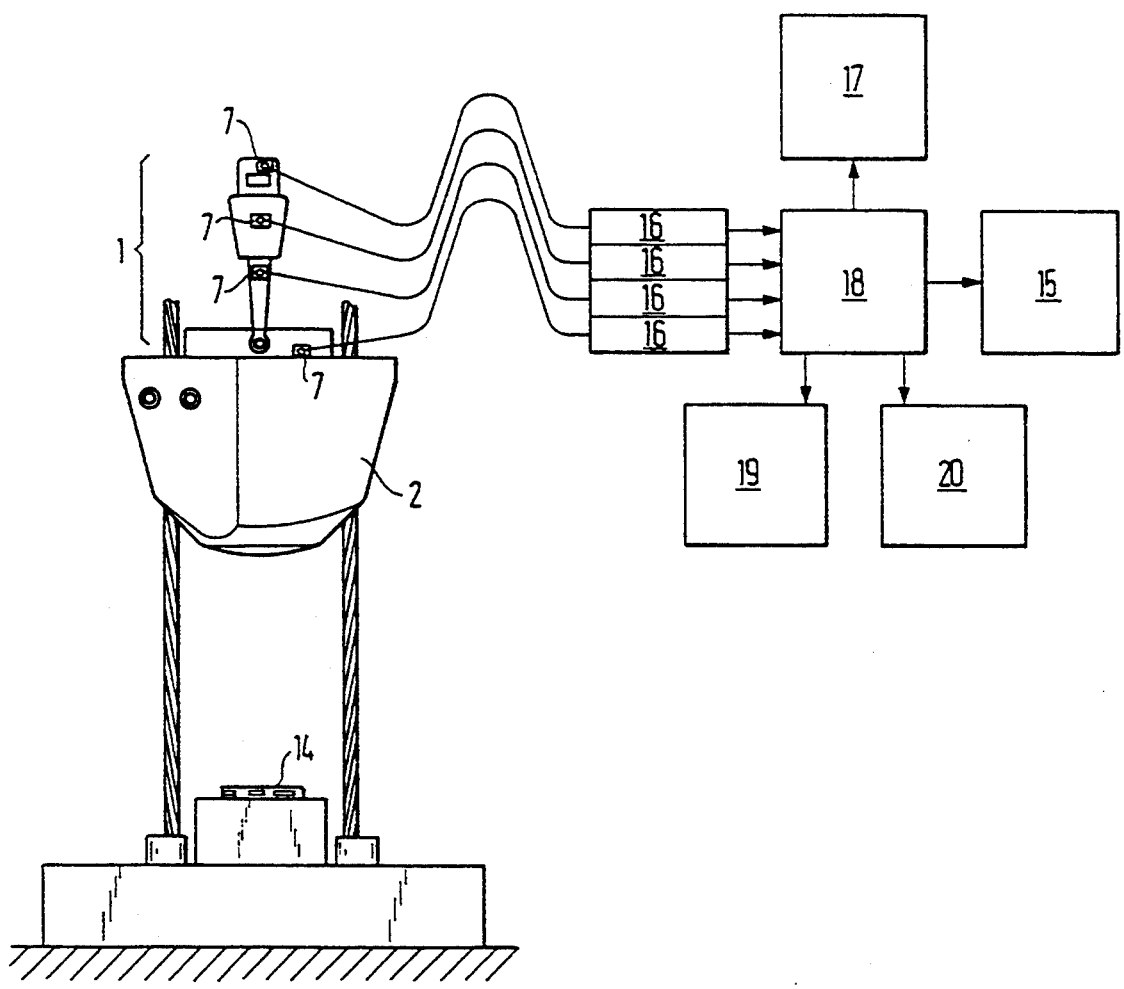
FIG. 2 is a schematic view of the apparatus as shown in FIG. 1 attached to associated recording and evaluation equipment.

The base shock at the drop carriage 2 and at the functional elements 4, 5, 6 is measured by means of the shock-acceleration transducers 7, which are preferably piezoresistive in nature. The output signals of the acceleration transducers 7 pass through amplifiers 16 and are subsequently input to a computer with analog-to-digital converter 18 and stored in an external digital memory 15 for further evaluation. The measurement signals are also displayed on a monitor 17 and can be printed out by means of a printer 19 and a plotter 20, as shown in FIG. 2.

Depending on the specimen to be tested, it may be important which end of the specimen 1 is fixed to the drop carriage 2. When such position-dependence exists, several series of measurements should be carried out with the specimen arranged in various position, for example both upside down and in reverse.

We claim:

1. A method for testing a device, wherein said device comprises at least a first part and one further part, said method comprising the steps of:
   coupling said first part of said device to shock loading means;
   applying a predetermined reproducible shock loading by said shock loading means to said device; and
   measuring a response acceleration of said shock loading means and of at least one of said first part or of said one further part of said device during shock loading.

2. Apparatus for dynamic testing of a device, wherein said device includes at least a first part and one further part, said apparatus comprising:
   loading means for application of a predetermined reproducible shock loading to said device, said loading means comprising a drop carriage and coupling means for coupling said first part of said device to said drop carriage; and
   acceleration measuring means comprising at least one acceleration transducer being attached to said drop carriage for measuring acceleration of said drop carriage during shock loading, and at least one further acceleration transducer being attached to at least one of said first part or said one further part of said device.

3. Apparatus as claimed in claim 2, further comprising a signal-processing system for the recordal, processing and display of output signals from said at least one acceleration transducer.

4. Apparatus as claimed in claim 2, wherein the drop carriage is constructed as an integral unit substantially in one piece.

5. Apparatus as claimed in claim 2, wherein the drop carriage is substantially conical in shape.

6. Apparatus as claimed in claim 2, wherein the drop carriage is constructed so that it is substantially symmetrical about its vertical axis.

7. Apparatus as claimed in claim 2, wherein a bottom portion of the drop carriage defines a rounded impact surface of part-spherical section.

8. Apparatus as claimed in claim 7, wherein said rounded impact surface has a radius in the range of 150 mm to 200 mm.

9. Apparatus as claimed in claim 7, wherein an upper portion of the drop carriage defines a cavity which is located so that the center of gravity of the drop carriage is shifted toward its impact surface.

10. Apparatus as claimed in claim 2, wherein the drop carriage is mounted by means of vertical guides and built-in slide bushes.

11. Apparatus as claimed in claim 2, wherein the drop carriage is made of a low-alloy, tempered steel.

* * * * *